(12) United States Patent
Ahmed et al.

(10) Patent No.: US 9,237,989 B2
(45) Date of Patent: Jan. 19, 2016

(54) COATING METHOD

(75) Inventors: Rehan Ahmed, Edinburgh (GB); Gerardus Hendricus Markx, Kirknewton (GB)

(73) Assignee: Taragenyx Limited, Glasgow, Scotland (GB)

( * ) Notice: Subject to any disclaimer, the term of this patent is extended or adjusted under 35 U.S.C. 154(b) by 1036 days.

(21) Appl. No.: 13/322,226

(22) PCT Filed: May 28, 2010

(86) PCT No.: PCT/GB2010/001073
§ 371 (c)(1),
(2), (4) Date: Feb. 20, 2012

(87) PCT Pub. No.: WO2010/136777
PCT Pub. Date: Dec. 2, 2010

(65) Prior Publication Data
US 2012/0141775 A1  Jun. 7, 2012

(30) Foreign Application Priority Data
May 28, 2009  (GB) .................................. 0909183.6

(51) Int. Cl.
*B32B 5/16* (2006.01)
*B05D 7/24* (2006.01)
(Continued)

(52) U.S. Cl.
CPC .............. *A61K 6/0067* (2013.01); *A61K 9/1676* (2013.01); *A61K 31/43* (2013.01); *B22F 1/02* (2013.01); *B22F 1/025* (2013.01); *C09D 1/00* (2013.01); *C23C 4/065* (2013.01); *C23C 24/04* (2013.01); *Y10T 428/25* (2015.01);
(Continued)

(58) Field of Classification Search
CPC .............. B05D 1/12; B22F 1/02; C23C 4/127
USPC .......................................... 427/180, 2.1–2.31
See application file for complete search history.

(56) References Cited

U.S. PATENT DOCUMENTS

| 3,655,425 A |   | 4/1972 | Longo et al. |
|---|---|---|---|
| 5,441,536 A | * | 8/1995 | Aoki et al. .................... 427/2.27 |

(Continued)

FOREIGN PATENT DOCUMENTS

| EP | 1411141 | 4/2004 |
|---|---|---|
| EP | 2258502 A1 | 12/2010 |

(Continued)

OTHER PUBLICATIONS

Int'l Search Report and Written Opinion issued in app. No. PCT/GB2010/001073 (2010).

(Continued)

*Primary Examiner* — Cachet Sellman
(74) *Attorney, Agent, or Firm* — Leydig, Voit & Mayer, Ltd.

(57) ABSTRACT

A method of coating an article includes the steps of providing a powder comprising coated particles; and spray coating the powder onto a surface of the article to form a composite coating. The spray coating may be carried out by combustion spraying, gas plasma spraying, including vacuum plasma spraying (VPS), and cold spraying. The article may be an implant for surgical or dental use. The powder may include particles of metal coated calcium phosphates, especially metal coated hydroxyapatite. The particles may include bioactive agents.

13 Claims, 3 Drawing Sheets

(51) Int. Cl.
    *A61K 6/00* (2006.01)
    *B22F 1/02* (2006.01)
    *C23C 4/06* (2006.01)
    *C23C 24/04* (2006.01)
    *A61K 9/16* (2006.01)
    *A61K 31/43* (2006.01)
    *C09D 1/00* (2006.01)

(52) U.S. Cl.
    CPC .......... *Y10T428/252* (2015.01); *Y10T 428/254* (2015.01); *Y10T 428/256* (2015.01); *Y10T 428/258* (2015.01); *Y10T 428/2991* (2015.01)

(56) References Cited

U.S. PATENT DOCUMENTS

| | | | |
|---|---|---|---|
| 5,631,044 A * | 5/1997 | Rangaswamy et al. | 427/216 |
| 5,876,793 A | 3/1999 | Sherman | |
| 6,344,276 B1 | 2/2002 | Lin et al. | |
| 6,582,763 B1 | 6/2003 | Nishimura et al. | |
| 6,846,853 B2 | 1/2005 | Shimp | |
| 6,974,532 B2 | 12/2005 | LeGeros et al. | |
| 7,344,749 B2 | 3/2008 | Becker et al. | |
| 7,348,060 B2 | 3/2008 | Tanaka et al. | |
| 7,635,515 B1 | 12/2009 | Sherman | |
| 2005/0234114 A1 * | 10/2005 | Lee | 514/365 |
| 2007/0166478 A1 | 7/2007 | Itsukaichi | |
| 2009/0306673 A1 | 12/2009 | Buma et al. | |
| 2011/0039024 A1 * | 2/2011 | Jabado et al. | 427/201 |

FOREIGN PATENT DOCUMENTS

| | | |
|---|---|---|
| JP | 8-253851 | 10/1996 |
| JP | 2001-270709 A | 10/2001 |
| JP | 2004-075445 A | 3/2004 |
| RU | 2039124 | 7/1995 |
| WO | 97/30797 | 8/1997 |
| WO | WO 9730797 A1 * | 8/1997 |
| WO | WO 2007033936 A1 * | 3/2007 |
| WO | 2008/056987 | 5/2008 |

OTHER PUBLICATIONS

Australian Patent Office, Patent Examination Report No. 2 in Australian Patent Application No. 2010252810, Oct. 14, 2015, 5 pp.

United States Patent Office, Office Action in U.S. Appl. No. 14/084,103, filed Sep. 23, 2015, 18 pp.

* cited by examiner

COATING METHOD

CROSS REFERENCE TO RELATED APPLICATIONS

This application is a U.S. nationalization under 35 U.S.C. §371 of International Application No. PCT/GB2010/001073, filed May 28, 2010, which claims priority to United Kingdom application no. GB 0909183.6, filed May 28, 2009. The disclosures set forth in the referenced applications are incorporated herein by reference in their entireties.

FIELD OF THE INVENTION

This invention relates to a method of spray coating articles using coated particles. The invention is especially concerned with methods that provide articles with suitable coatings for use in a variety of applications including biocompatible implants.

BACKGROUND TO THE INVENTION

Coating articles by spraying with solid particles or powders is a useful technique that can have a number of advantages over other techniques such as coating with a suspension or solution of the coating material and then drying or curing to provide a coated surface.

In spray coating techniques the particles are propelled, at a high velocity, so that they adhere firmly to a article surface and adhere to each other to form the coating layer. Generally the particles impact on the surface and deform significantly. The "splats" formed by the impacting particles build up to form a surface coating in a controlled manner allowing the thickness of the coating to be selected. Reasonable adhesion of the splats to the article can be achieved in many instances. For example with metal particles impacting on a metal article surface it is believed that dislodging of the surface oxide layer on the metal article and the metal particles results in metal (particle) to metal (article) bonding occurring.

Bonding can also be achieved between dissimilar particle and article materials. For example, for biocompatible implants, coating a generally metallic article (implant) with hydroxyapatite is an attractive proposition as it affords the prospect of providing an implant that is compatible with bone, and should more readily bind to or assimilate with the patients own bone tissue.

Current techniques used to provide hydroxyapatite (HA) coatings on articles such as titanium implants can make use of the thermal spraying technique (such as plasma spray). Other techniques such as, ion beam, magnetron and plasma sputtering processes are also known. Pulsed laser deposition has also been attempted. Thermal spraying is a line of sight process where coating powder particles are heated (at up to the melting point of the particles) and propelled at high velocity (typically 600~800 ms$^{-1}$ or even 400-1000 ms$^{-1}$) on the underlying material to form a coating. The particles form a coating by mechanically interlocking together as they impact and deform on the surface being coated.

Despite the commercial attractiveness and viability associated with the use of thermal spray technology for HA coating deposition, there are important challenges, which have hindered its widespread use. The bonding between the coating and the substrate and between the splats forming the coating layer is not reliable.

The risks associated with poor coating quality are quite high. A detached coating can result in loss of functionality of the implant. Detached coating particles can cause abrasion of the joint between the implant and natural tissue or bone mineral.

Efforts to overcome the problem of poor HA coating adhesion to a metallic (titanium or titanium alloy) article have included, as summarised in U.S. Pat. No. 6,344,276, the deposition of composite coatings where a metallic layer or layers has been applied during the coating process as a pre-coat or top coat. Alternatively composite metallic/HA coatings may be applied in various ways. In U.S. Pat. No. 6,344,276 further methods for providing a hydroxapatite containing coating, which has a low dissolution rate, are described. The method involves forming a composite target of titanium (10-75% by volume) and hydroxyapatite (90-25% by volume) by cold pressing a powdered mixture of the two components. The composite target is then deposited on titanium or titanium alloy surfaces by using ion sputtering, laser ablation, or vapour deposition techniques. The resulting coating comprises an amorphous hydroxapatite/titanium layer.

Despite the various techniques described above there is still a need for further improved coating techniques especially in the demanding field of biocompatible implants.

For example rather than using a hydroxapatite-coated titanium implant in dental work it is current practice to make use of titanium implants without such coatings. The titanium dental implant is instead provided with a roughened surface. Typically such an implant is inserted into tooth/jaw and covered to protect it from damage for a period of from 2 to 6 months to allow bonding between the natural tissues/bone and the implant to occur. The implant is then used, for example as the foundation for a tooth crown. Hydroxapatite coatings should in principle allow more rapid bonding to the subject but the risk of loss of such coatings from the implant surface is generally regarded as unacceptable.

It is an object of the present invention to provide coating methods that avoid or at least alleviate one or more of the aforementioned difficulties

DESCRIPTION OF THE INVENTION

According to a first aspect the present invention provides a method of coating an article comprising the steps of:
  providing a powder comprising coated particles; and
  spray coating the powder onto a surface of a said article to form a composite coating.

The powder employed in the method of the invention comprises coated particles. Generally the particles are completely covered in the coat material. The particles have a core of one material, which is encapsulated in the coat, which comprises another material. However, if desired both the core and the coat may comprise more than one material and there may be more than one coat applied to each particle.

Methods of particle coating that can be used to provide the coated particles for the method include but are not limited to chemical or physical vapour deposition (PVD), electroplating, or dip coating. Vapour deposition (PVD) is particularly useful in many cases, for example in coating ceramic particles with a metal where the technique can provide metal coated or encapsulated particles with an even layer of the metal of a controlled thickness.

The combination of vapour deposition to coat particles and then spray coating with a powder comprising the coated particles provides an effective method of spray coating many articles. The method gives useful coatings comprising a well-mixed matrix of the particle core material and of the particle coat material.

For example titanium coated hydroxyapatite particles can be made by vapour deposition of titanium on hydroxyapatite as described hereafter with reference to a particular example and the resulting coated particles used to spray coat a surface of an article.

It has been found that hydroxyapatite particles can be individually coated with titanium or titanium alloy by using vapour deposition techniques that include means to prevent aggregation of the particles during processing. For example a vibrating table, rotating cup or tumble drier, each of which agitates the particles during the deposition process.

It will be understood that even in manufacture intended to provide a fully encapsulating coating, the coating on some particles in a sample may not be complete. Furthermore for some applications a partial or incomplete coating of particles may be sufficient or even desirable. For example, where the resultant spray coating on the article surface is to have a relatively low amount of the particle coating material.

The particle core material may comprise or consist of materials selected from the group consisting of ceramics, polymers, metals and combinations thereof. The particle coat material may also comprise or consist of materials selected from the group consisting of ceramics, polymers, metals and combinations thereof. Other materials may be included in a particle core or a particle coat, such as inorganic salts or organic compounds. In some cases particle cores or coats may consist of a chosen inorganic salt or organic compound.

It will be appreciated that to obtain the benefits of using coated particles the coat and the core will be of different compositions, although they may contain components common to both. The use of a metal as core or coating has the advantage of providing a degree of ductility to the particles when they impact on the surface of the article or with each other in the coating layer as it forms.

A metal coating on particles has additional benefits. In spray coating techniques the particles are subjected to high stress, albeit for a short period of time. This can include high temperatures, up to 2000° C. or even more, and the collision and deformation on impact with the surface being coated. The resulting coating can have both micro- and macro-residual stress present due to the impact forces. A metal coating on the particles can help relax these stresses due to its ductility. The metal matrix within the microstructure of the manufactured composite coating can allow relaxation of stress.

A metal coating on particles can act to protect or at least partially shield the particle core from these stresses during the coating process. This can result in a coated surface including the particle core material with unchanged or substantially unchanged physical properties, in comparison with the core material before spraying.

For example, where hydroxyapatite containing coatings are applied to biomedical implants, it is generally regarded as desirable that the hydroxyapatite is present in a crystalline form. Such a coating is considered to be superior to an amorphous hydroxyapatite coating. It is suggested that the amorphous coating dissolves too quickly when implanted in a subject to allow time for the natural tissues, such as bone, surrounding the implant to develop and grow in a manner that will produce the desired close integration of the implant with the subjects natural tissue(s).

Examples of ceramic materials that may be employed include but are not limited to calcium phosphates such as apatites, especially hydroxyapatite (HA), alumina ($Al_2O_3$), silica ($SiO_2$) and tungsten carbide (WC). Calcium phosphate minerals such as apatites especially hydroxyapatite are of particular use in providing coatings suitable for surgical implants. Examples of metals that may be employed include but are not limited to titanium, titanium alloys, cobalt, chromium and alloys such as NiCrBSi. Titanium alloys may include Ti-6Al or Ti-6Al-4V. Examples of polymers that may be employed include but are not limited to UHMWPE (Ultra High Molecular Weight Polyethylene), PTFE and PEEK.

The choice of particle core material and of particle coat material depends on the article to be spray coated and the application envisaged for the spray-coated article.

For biocompatible implants for use in dental or bone applications calcium phosphates such as apatites, for example hydroxyapatite, particle cores may be used. The apatite may be amorphous or crystalline when used in the method of the invention. As noted above crystalline hydroxyapatite is often preferred for implants. The particle coat may be of a metal especially when the article (e.g. implant body) is itself of a metal or has a metal surface. The metal particle coat may be of titanium or a titanium alloy. When used to spray coat an article such particles provide splats wherein the metal particle coat gives strong bonding to the metal surface of the article. The core material that may be of an apatite, for example, allows for rapid bonding/assimilation into bone or tooth when the implant is used. Thus a metal/calcium phosphate, for example a metal/apatite, advantageously a metal/hydroxyapatite, especially a titanium or titanium alloy/hydroxyapatite composite coating is provided.

An advantage of using the coated particles of the invention in a spray coating method is that each individual particle arriving at the article during spraying carries with it a controllable amount of core material and of coat material, to a desired ratio. Thus at the impact site of each individual particle a calculated amount of both particle core material and particle coat material is laid down on the article surface or on the coating layer being built up on the surface. Spray coated articles prepared by the method of the present invention can thus have a composite coating with a relatively even distribution of both the particle core and particle coat materials. The method provides an exceptionally intimately and controllably mixed composite coating which can be selected to adhere well to chosen surfaces of an article and provide desirable functionality.

The coated particles tend to deform substantially (form a splat) on impact during spray coating of an article. Therefore even though the core material of the particles may be encapsulated in the coat material, both materials will be exposed on impact and form a matrix of the two materials with the other splats as the coating is built up on the article. Thus in many cases where two materials are selected for the composite spray coating either material may be used as the core with the other being used as the coat of the coated particles.

For simplicity in manufacture where one material is to form the bulk of the spray coating it will generally be used as the core. A relatively thin layer of the other material can then be applied to coat the cores to form particles of the desired composition.

The method of the invention may be extended to include using coated particles that have two or more coatings applied, allowing the formation of a spray coating on the article that comprises a matrix of more than two different materials.

For biocompatible implants preferred spray coatings include metal/calcium phosphate, metal/apatite, for example titanium or titanium alloy/hydroxapatite composites as mentioned above. Thus according to a second aspect the present invention provides particles suitable for use in spray coating an article, said particles comprising;

a calcium phosphate core and a metal coating; or
a metal core and a calcium phosphate coating.
The particles may comprise;
an apatite core and a metal coating; or
a metal core and an apatite coating.

Advantageously a metal coated calcium phosphate core (typically of an apatite such as hydroxyapatite) particle is employed and the metal coating can protect the core form thermal stress during a spray coating process.

A thickness of up to 10 μm for the metal particle coatings may be employed. Even thicker particle coating layers may be envisaged but often a thin layer or even a very thin layer may be advantageous. The thickness of coating on the particles can be selected for a given application, and adjusted readily by amending the particle coating process. For some applications it may be desirable to have a thin metal coating on particles just sufficient to provide the benefits of creating a metal matrix holding the core material (e.g. a ceramic such as hydroxyapatite) together in a strong coating layer on a substrate (e.g. a metal). The coating formed on the substrate will then largely behave as if a coating of only the core material, except for the superior adhesion provided by the metal matrix produced on impact of the coated particles onto the substrate.

The spray coating technique employed may be selected from the group consisting of combustion spraying, gas plasma spraying and cold spraying. All three techniques are well known in the field of spray coating. The choice of technique may depend on the type of coated particles, any other components of the powder and on the article being coated. For example where the particles carry biologically active agents as described hereafter then cold spraying may be preferred if the active agents are particularly delicate, to avoid damage to the agents and their activity. However biologically active agents may be spray coated by the other techniques. For example thermal spraying, when the residence time in the hot gas (or flame) of powders including the biologically active agents may be short, thus avoiding or minimising decomposition.

Where the particles employed are metal coated particles, for example metal coated calcium phosphate (for example hydroxyapatite) particles the active agents, especially biologically active agents, that are often sensitive to thermal stress may be conveniently contained in a layer inside the (outermost) metal coating or, if the particle core is porous, within the core material. Even if the core material is not porous it may be possible to mix the active agent with a core material (e.g. where the core material is a mouldable polymer) to incorporate the active agent within the core.

Advantageously porous particle cores may be impregnated with an active agent after the particle cores have been coated. This can be done where the coating on the particles is partial or porous in nature. This approach avoids subjecting the active agent to the stress of the particle coating process, which may include a considerable period at an elevated temperature for particles coated with a metal by a vapour deposition process.

The approach of providing a metal coating to particle cores containing an active agent can protect thermally sensitive active agents from exposure to heat during a spraying process. Following spraying the active agent is available for use as the formation of splats exposes the cores of particles.

In addition, where the coating applied to the particle cores is porous the active agent can be released even where the particle core material is covered by the particle coating material.

The temperature and velocity at which the coating process is carried out, is also dependent on the nature of the coated particles, other components in the powder and the article. The temperature employed may be in the range of from 0° C. to as much as 3000° C. Lower or higher temperatures may be appropriate for the production of some coatings. Generally the temperature is kept below the melting point, decomposition point or any other temperature where functionality of a component of the particles being employed may be degraded. Thermal spraying is advantageous when the coated particles and/or the article surface comprises a metal as the heat assists in softening the metal(s) employed, thus aiding the bonding process when the particles impact on the article to form splats.

The velocity at which the particles are sprayed onto the article is sufficient to cause bonding to occur given the nature of the powder, the article surface, the coating technique and conditions employed. A velocity in the range of from 100 $ms^{-1}$ to 2000 $ms^{-1}$ may be employed.

The coated particles are generally provided in a selected size range, to assist in controlling the spray coating process thereby providing a spray coated layer of the desired physical characteristics. A coated particle size of from 1 μm to 300 μm, even 1 μm to 150 μm, desirably 10 μm to 45 μm may be employed for many applications, providing particles that are readily sprayed by the various spray coating techniques mentioned above. Other components in the powder, if present, may conveniently be provided in the same size range.

Alternatively the coated particles may be nanoparticles, which can be aggregated to form larger particles (clusters) if required by the nature of the materials and the spraying process employed.

The powder for spray coating onto the article may further comprise chemically or biologically active agents. This allows the production of a spray-coated article with additional functionality. The active agents may be incorporated in the coated particles, for example in the particle core material, the particle coat material or in both. Alternatively the powder may comprise additional particles that comprise or consist of the active agents.

Particles of active agents or comprising active agents may themselves be coated, for example by vapour deposition with a metal to assist in their integration with the spray coating matrix. As a yet further alternative the active agents may be provided as a separate coat on the coated particles. This may be the outermost coat or an inner coat of the coated particles.

For medical applications, such as implants, the active agents contemplated may be considered to be "bioactive" agents. That is to say they may be agents that interact with a human or animal subject's physiology or act to treat a disease condition or a potential disease condition. In some cases they may be selected to assist in the integration of an implant into a subject's body.

Examples of active agents (bioactive agents) that may be employed include but are not limited to antibiotics, which could be included to fight or prevent infections, drugs (e.g. antitumor drugs, anti-inflammatory agents), adhesion factors such a fibronectin, and growth factors and morphogens such as the Bone Morphogenetic Proteins (BMPs). In addition other components may be used, for example agents ("slow release agents") to moderate the release of the active agents and stabilizers, to prevent degradation of the active agents, such as are well known in the art.

The method of the invention provides useful coated articles such as bioimplants (implants for surgical or dental use) and provides useful functional coatings on other articles employed in a wide variety of other uses. For example thermal barrier coatings, wear resistant coatings and coatings on fuel cell components such as membranes.

Thus according to a third aspect the present invention provides an article comprising a spray-coated surface obtainable by the steps of:
  providing a powder comprising coated particles; and
  spray coating the powder onto a surface of a said article to form a composite coating.

Advantageously the coated particles have a coating that comprises a metal. As discussed above a metal coated particle has advantages including helping to preserve the integrity and physical state or properties of the core material employed.

However, for some applications the opposite arrangement may be preferable. For example where the resistance to wear that can be provided by a ceramic material is important, metal cored particles having a vapour deposited ceramic layer may be desireable.

BRIEF DESCRIPTION OF THE DRAWINGS

Further preferred features and advantages of the present invention will appear from the following detailed description given by way of example of some preferred embodiments illustrated with reference to accompanying drawings in which.

DETAILED DESCRIPTION OF THE DRAWINGS AND OF SOME EXAMPLES ILLUSTRATING EMBODIMENTS OF THE INVENTION

Figure 1:
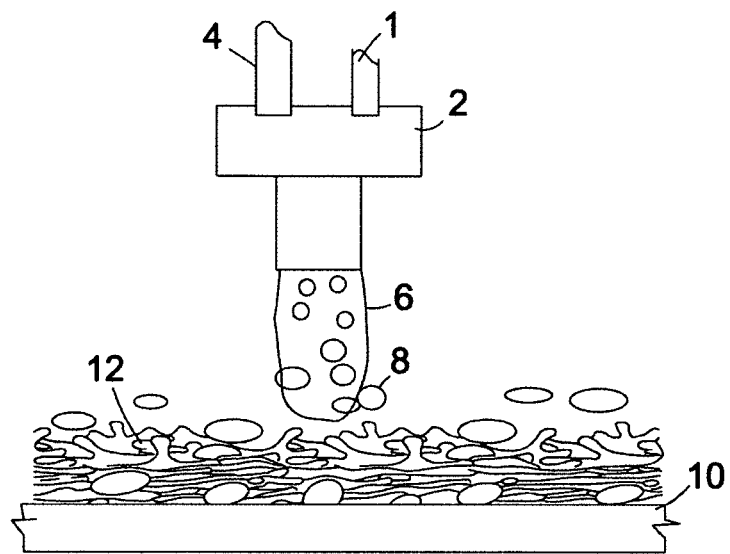
FIG. 1 illustrates schematically a thermal spray coating process.

FIG. 1 illustrates schematically a thermal spray coating process suitable for applying the coated particles of FIG. 2 (discussed below) to a surface. In FIG. 1 a powder 1 (e.g. the particles of FIG. 2) is introduced into a spray nozzle 2 together with a fuel 4. The fuel is ignited to produce a hot flame 6 (at a temperature of up to 2500° C.) whose expansion from the nozzle 2 both heats and accelerates a spray 8 of powder towards a surface 10. At the surface 10 the impacting powder particles form splats (collision deformed particles) that bond to the surface 10 and to each other to form a coating 12 which builds up on the surface.

The surface 10 may be of a titanium dental implant for example. Other thermal spraying techniques may be employed, for example spraying the powder 1 through the nozzle 2 by means of a heated gas stream rather than by flame. If desired, for example where the powder comprises delicate bioactive agents, a cold spray technique may be used where the flame 6 or hot gas flow is replaced with a cool gas flow. Plasma spray techniques such as are known in the art may also be employed.

Figure 2A:
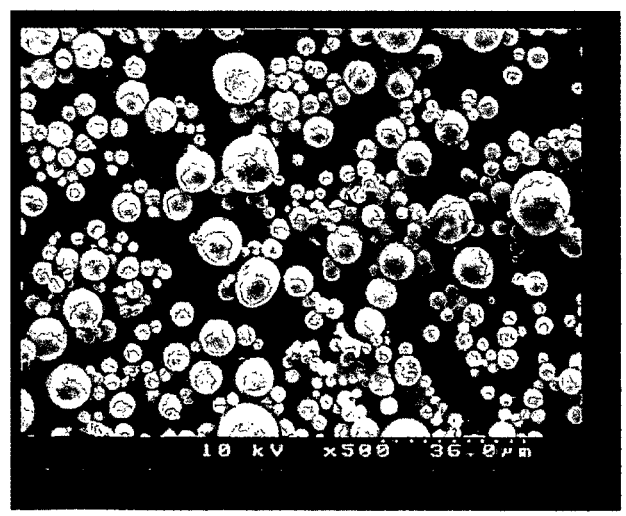
FIGS. 2a, 2b show microscope images of coated particles.

FIG. 2a shows a microscope image of nano-composite hydroxyapatite particles, which have been coated with titanium by a vapour deposition process. As can be seen from the image the individual particles are in general separate, the metal coating process has not caused significant aggregation of the sample. This makes the particles suitable for spray coating processes, for example the thermal spray coating process illustrated in FIG. 1. The particles shown were prepared from hydroxyapatite powder which contained spherical particles with a size range of from 2 µm to 10 µm before vapour deposition of the titanium. Hydroxyapatite particles with this size range are commercially available or can be manufactured by methods well known in the art, and then subjected to the vapour deposition procedure.

Figure 2B:
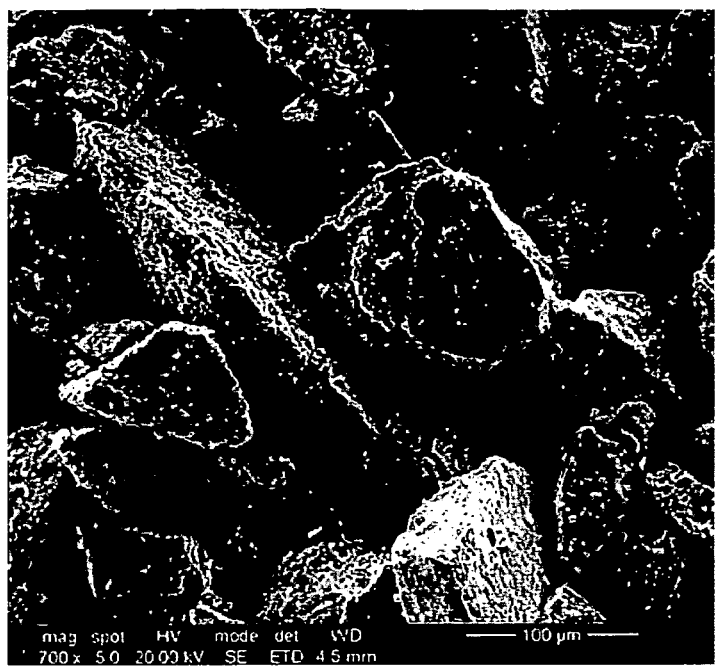

FIG. 2b shows larger titanium coated hydroxyapatite particles (size range by laser diffraction=125±45 µm) prepared in a similar fashion. The particles have a thin titanium coating (less than 1 µm). These particles were used to prepare the coatings of FIGS. 3 and 4.

Figure 3:
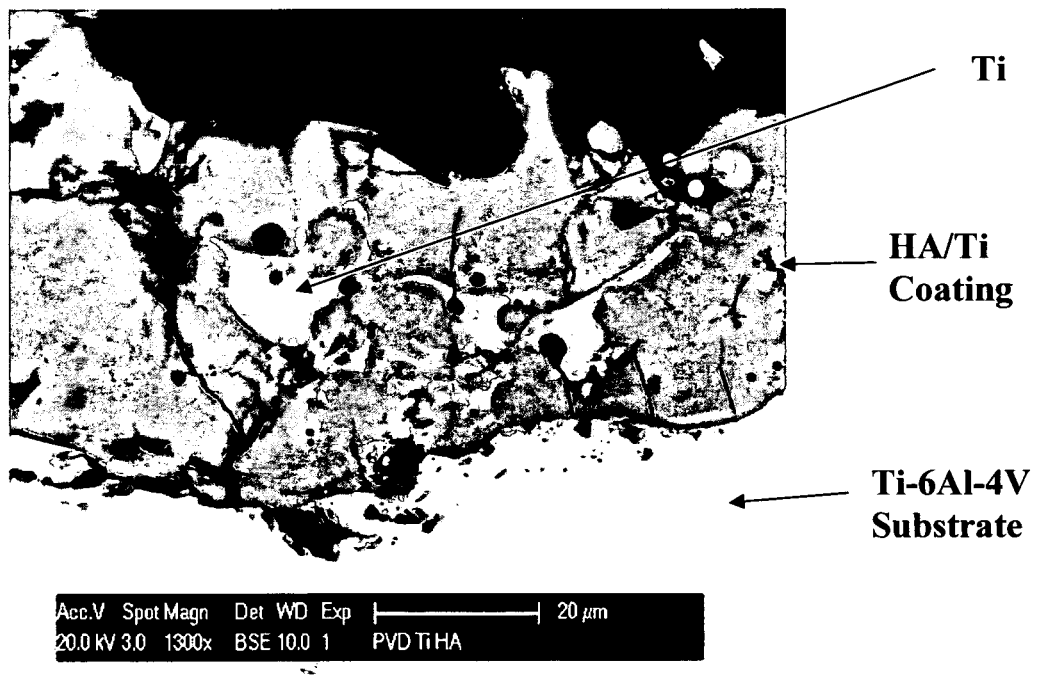
FIG. 3 shows an SEM micrograph of a spray coating on a substrate.

FIG. 3 shows a cross section of a metal alloy (Ti6Al4V) substrate coated with a layer of hydroxyapatite/titanium (HA/Ti) formed by a typical vacuum plasma spray (VPS) process making use of the titanium coated hydroxyapatite particles of FIG. 2b.

The particles employed had size range of 125±45 µm by laser diffraction and the titanium coating was applied by a physical vapour deposition (PVD) method to produce a thickness of coating on the particles of the order of less than 1 µm.

VPS spray coating the substrate was carried out at a pressure of 200-300 mbar at a current of 550-700 Amps using argon (flow rate 30-40 l/min and nitrogen (flow rate <10 l/min) to produce the coated substrate shown in the figure.

Under these conditions the plasma temperature will typically be in excess of 2000° C. and the particles themselves may be expected to reach around 1700° C. Although this is higher than the melting point of hydroxyapatite the brief exposure to the high temperature and some protection afforded by the titanium layer coating the particles results in a good quality coating.

The coated substrate shown has a coating of about 30-40 µm thickness and shows regions of hydroxyapatite with titanium regions between them, forming a matrix. X-ray diffraction confirmed that the crystallinity of the hydroxapatite, present in the original particles, had been maintained in the spray coating.

The exemplary coating had a surface roughness ($R_{ZDIN}$ 45.95±3.51 µm) that is regarded as satisfactory for an implant where a rough surface provides better integration with natural tissue.

Tensile testing of the coating according to BS ISO 13779 (a standard for hydroxyapatite coatings on implants intended for surgical use) gave a strength of the coating to the substrate of between 43.35 MPa and 52.13 MPa (average 47 MPa). This result exceeds the expectations of BS EN ISO 13779-2 (a minimum tensile strength of 15 MPa) by almost 300%.

There were some indications that the actual coating strength may be even higher than found by the standard test. The test utilises an epoxy adhesive to bond a piece of uncoated substrate to the coating of apiece of the coated substrate. This assembly is then pulled apart in a tensile tester to measure the coating strength, but in this case the results are close to the strength of the adhesive employed (66.73 MPa). Therefore it is possible that failure of the assembly was initiated in the epoxy adhesive and the bulk of the coating has an actual bond strength higher than that indicated by the test.

Inspection of the coating suggests that at least some of the strength of the coating is provided by the regions of titanium that can act to stop a crack propagating in the hydroxyapatite.

Thus a strongly bonded coating was prepared by the methods described.

Figure 4:
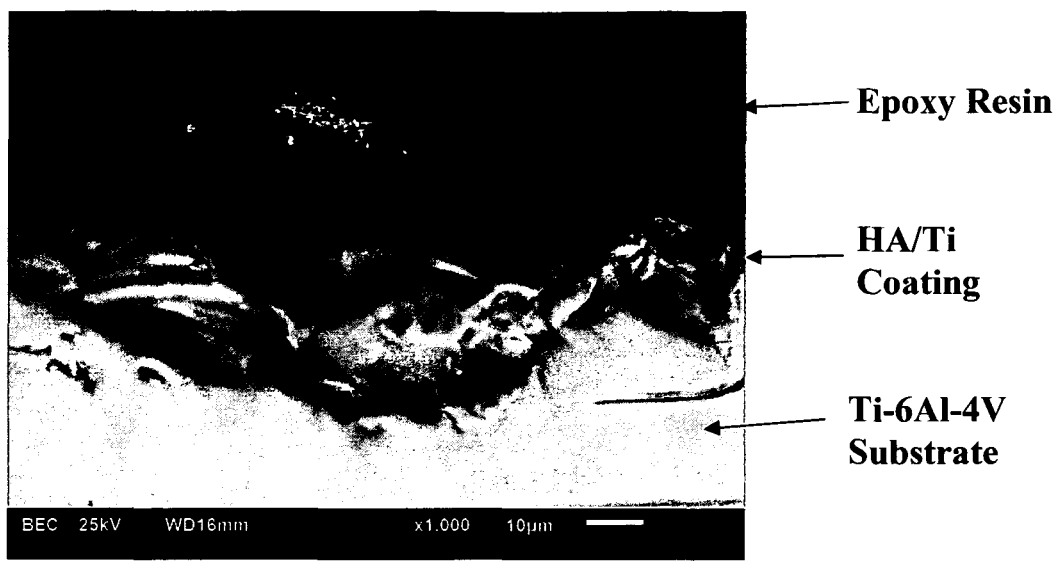
FIG. 4 shows an SEM of a coating formed by a different spray technique on a substrate.

FIG. 4 shows a coating on a substrate similar to that of FIG. 3 but prepared following a cold spray technique.

Titanium coated hydroxyapatite particles, similar to those employed in the VPS technique used to provide the coating shown in FIG. 3, were again used.

The coating conditions employed were as follows:
Gases: helium and air (98% He)
Pressure: 1.4 MPa (14 bar pressure of working gas, 15 bar pressure of feeder gas)
Heating current: 345 A (giving a temperature around 500° C.)

The coated particles were sprayed through a stainless steel nozzle at a distance of 15 mm. The resulting coating shows good bonding with no signs of cracks and negligible porosity.

Coated particles used to prepare coatings on substrates may also include active agents. The viability of such agents has in coated particles has been demonstrated by impregnating porous silica particles (crushed pellets sieved to provide particles of approximately 150 μm) with the anti-biotic ampicillin (Sigma-Aldrich) as follows:

10 g silica particles, 10 g deionised water and 1.5 g ampicillin were mixed and the silica particles dried at 80° C. for 0.5 hours followed by air drying for 3 hours. The particles were then subjected to a PVD coating treatment similar to that described above for the hydroxyapatite particles to produce titanium coated silica particles containing the ampicillin.

Contacting the particles to an agar plate infected with *Micrococcus luteus* (*M. luteus*) showed that the ampicillin had retained its antibiotic activity, as seen by a ring of non growth/lysis around the site of contact. This effect obtained despite the harsh conditions of the titanium coating process (100 to 200° C. for ~4 hours and the considerable temporal and spatial temperature gradients inherent in the process). This effect was seen both where the particles had been crushed, to ensure that any viable antibiotic contained inside the metal coating would be released, and without crushing the particles. Thus it was demonstrated that the ampicillin could leach through the titanium outer coating i.e. the coating was porous.

The invention claimed is:

1. A method of coating an article comprising the steps of:
   providing a powder comprising coated particles; and spray coating the powder onto a surface of said article to form a composite coating,
   wherein the article core comprises or consists of a calcium phosphate and the coated particles comprise a metal coating.

2. The method of claim 1 wherein the metal coating comprises or consists of titanium or a titanium alloy.

3. The method of claim 1 wherein the coating on the coated particles has been formed by a vapour deposition process.

4. The method of claim 1 wherein the spray coating technique employed is selected from the group consisting of combustion spraying, gas plasma spraying, and cold spraying.

5. The method of claim 4 wherein the gas plasma spraying is vacuum plasma spraying.

6. The method of claim 1 wherein the particle core comprises or consists of hydroxyapatite.

7. The method of claim 1 wherein the powder for spray coating further comprises a bioactive agent.

8. The method of claim 7 wherein the bioactive agent is incorporated in the coated particles.

9. The method of claim 8 wherein the bioactive agent is incorporated in the particle core material.

10. The method of claim 9 wherein the bioactive agent is incorporated in the particle core material by:
    mixing the bioactive agent with core material when forming the cores; or
    impregnating porous cores with the bioactive agent before coating to form coated particles; or
    by impregnating porous cores of coated particles with the bioactive agent, when the particle coating is partial or is porous to the bioactive agent.

11. The method of claim 7 wherein the bioactive agent is selected from the group consisting of antibiotics, anti-tumour drugs, anti-inflammatory drugs, adhesion factors, growth factors and morphogens.

12. The method of claim 11 wherein the adhesion factor is fibronectin.

13. The method of claim 11 wherein the growth factor is a Bone Morphogenetic Protein.

* * * * *

UNITED STATES PATENT AND TRADEMARK OFFICE
CERTIFICATE OF CORRECTION

PATENT NO. : 9,237,989 B2  
APPLICATION NO. : 13/322226  
DATED : January 19, 2016  
INVENTOR(S) : Ahmed et al.

Page 1 of 1

It is certified that error appears in the above-identified patent and that said Letters Patent is hereby corrected as shown below:

Claims

Column 9, Claim 1, line 5, "article" should read --particle--.

Signed and Sealed this
Twenty-sixth Day of April, 2016

Michelle K. Lee
*Director of the United States Patent and Trademark Office*